US006465439B1

(12) United States Patent
Nicklin et al.

(10) Patent No.: US 6,465,439 B1
(45) Date of Patent: Oct. 15, 2002

(54) PHARMACEUTICAL COMPOSITIONS

(75) Inventors: Paul Leslie Nicklin, Henfield; Judith Ann Phillips, Sevenoaks; William Guy Love, Horsham, all of (GB); Karen Ophelia Hamilton, Lawrence, KS (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/254,322

(22) PCT Filed: Sep. 3, 1997

(86) PCT No.: PCT/EP97/04796

§ 371 (c)(1),
(2), (4) Date: May 14, 1999

(87) PCT Pub. No.: WO98/09633

PCT Pub. Date: Mar. 12, 1998

(30) Foreign Application Priority Data

Sep. 4, 1996 (GB) ................................................ 9618376

(51) Int. Cl.$^7$ ..................... A61K 48/00; A61K 9/127; C12N 15/85; C07H 21/04
(52) U.S. Cl. ................. 514/44; 536/23.1; 536/24.31; 536/24.5; 424/450; 435/325; 435/375
(58) Field of Search ..................... 514/44; 536/23.1, 536/24.3, 24.33, 24.5; 435/6, 325, 375, 91.1; 424/450

(56) References Cited

U.S. PATENT DOCUMENTS

| 5,225,212 A | | 7/1993 | Martin et al. ................ 424/450 |
| 5,916,807 A | * | 6/1999 | Bennett et al. ............. 435/375 |

FOREIGN PATENT DOCUMENTS

| WO | WO 93/19203 | 9/1993 |
| WO | WO 95/02069 | 1/1995 |
| WO | WO 95/03788 | 2/1995 |

OTHER PUBLICATIONS

Stanley T. Crooke, Basic Principles of Antisense Therapeutics, Springer–Verlag, NY, p. 3., 1998.*

Baxter G. et al., Biochemistry, vol. 31, "PKCε Is Involved in Granulocyte–Macrophage Colony–Stimulating Factor Signal Transduction: Evidence from Microphysiometry and Antisense Oligonucleotide Experiments," pp. 10950–10954 (1992).

Busuttil S.J. et al., Journal of Surgical Research, vol. 63, "Antisense Suppression of Protein Kinase C–α and –§ in Vascular Smooth Muscle," pp. 137–142 (1996).

Coussens L. et al., Science, vol. 233, "Multiple, Distinct Forms of Bovine and Human Protein Kinase C Suggest Diversity in Cellular Signaling Pathways," pp. 859–866 (1986).

Dean N.M. et al., Journal of Biological Chemistry, vol. 269 (23), "Inhibition of Protein Kinase C–α Expression in Human A549 Cells by Antisense Oligonucleotides Inhibits Induction of Intercellular Adhesion Molecule 1(ICAM–1) mRNA by Phorbol Esters," pp. 16416–16424 (1994).

Dean N.M. and McKay R., PNAS USA, vol. 91, "Inhibition of protein kinase C–α expression in mice after systemic administration of phosphorothioate antisense oligodeoxynucleotides," pp. 11762–11766 (1994).

Farese R. et al., Antisense Research and Development, vol. 1, "Antisense DNA Downregulates Protein Kinase C Isozymes (β and α) and Insulin–Stimulated 2–Deoxyglucose Uptake in Rat Adipocytes," pp. 35–42 (1991).

Godson C. et al., Journal of Biological Chemistry, vol. 268 (16), "Inhibition of Expression of Protein Kinase C α by Antisense cDNA Inhibits Phorbol Ester–mediated Arachidonate Release," pp. 11946–11950 (1993).

Maier J. and Ragnotti G., Experimental Cell Research, vol. 205, "An Oligomer Targeted against Protein Kinase Cα Prevents Interleukin–1α Induction of Cyclooxygenase Expression in Human Endothelial Cells," pp. 52–58 (1993).

\* cited by examiner

*Primary Examiner*—John L. LeGuyader
*Assistant Examiner*—Janet L. Epps
(74) *Attorney, Agent, or Firm*—Woodcock Washburn LLP

(57) ABSTRACT

A pharmaceutical composition is disclosed comprising (A) and oligonucleotide having 5 to 50 nucleotide units, which is specifically hybridizable with DNA or RNA derived from a protein kinase C gene, entrapped in (B) sterically stabilized liposomes.

53 Claims, No Drawings

SEQUENCE LISTING

<160> NUMBER OF SEQ ID NOS: 53

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
ccccaaccac ctcttgctcc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 2
gttctcgctg gtgagtttca                                                    20

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: modified_base
<222> LOCATION: (1)..(20)
<223> OTHER INFORMATION: another oligo prepared with bases 1-20 having
      P=S linkages and bases 1-6 and 15-20 additionally
      having 2'-methoxy bases
<220> FEATURE:
<221> NAME/KEY: modified_base
<222> LOCATION: (1)..(20)
<223> OTHER INFORMATION: Bases 1-6 and 15-20 have P=O linkages and
      2'-methoxy nucleotides.  Bases 7-14 have P=S
      linkages.
<220> FEATURE:
<221> NAME/KEY: modified_base
<222> LOCATION: (1)..(20)
<223> OTHER INFORMATION: another oligo prepared with P=S linkages at
      bases 1,6-14 and 19, 2'-methoxy bases at bases 1-6 and
      15-20 and P=O linkages at bases 2-5 and15-18.
<220> FEATURE:
<221> NAME/KEY: modified_base
<222> LOCATION: (1)..(20)
<223> OTHER INFORMATION: another oligo prepared with 2'-methoxy bases at
      bases 1-6 and 15-20; P=S linkages at bases 1, 6,
      8, 10, 12-14 and 19; P=O linkages at bases 2-5, 7,
      9, 11 and 15-18.
<220> FEATURE:
<221> NAME/KEY: modified_base
<222> LOCATION: (1)..(20)
<223> OTHER INFORMATION: another oligo prepared with 2'propoxy
      nucleotides at bases 1-6 and bases 15-20; P=s linkages at
      bases 1-20.
<220> FEATURE:
<221> NAME/KEY: modified_base
<222> LOCATION: (1)..(20)
<223> OTHER INFORMATION: another oligo prepared with 2'-propoxy
      nucleotides at bases 1-6 and bases 15-20; P=S linkages at
      bases 6-14 and P=O linkages at bases 1-4 and 15-19.
<220> FEATURE:
<221> NAME/KEY: modified_base
<222> LOCATION: (1)..(20)
<223> OTHER INFORMATION: another oligo prepared with 2'propoxy
      nucleotides at bases 1-6 and 15-20; P=S linkages at bases 1,
      6-14 and 19; P=O linkages at bases 2-5 and 15-18.
<220> FEATURE:
<221> NAME/KEY: modified_base
<222> LOCATION: (1)..(20)
<223> OTHER INFORMATION: another oligo prepared with 2'-propoxy
      nucleotides at bases 1-6 and 15-20; P=S linkages at bases 1,
      6, 8, 10, 12-14 and 19; P=O linkages at bases 2-5,
      7, 9, 11 and 15-18.

<400> SEQUENCE: 3
aaaacgtcag ccatggtccc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 4
ggattcactt ccactgcggg                                              20

<210> SEQ ID NO 5
<211> LENGTH: 20
<212> TYPE: DNA
```

```
<213> ORGANISM: Artificial Sequence
<220> FEATURE:
<223> OTHER INFORMATION: Description of Artificial Sequence:synthetic
      oligonucleotide

<400> SEQUENCE: 5
gagaccctga acagttgatc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 6
cccgggaaaa cgtgagccat                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 7
ctgcctcagc gcccctttgc                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 8
agtcggtgca gtggctggag                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 9
gcagaggctg gggacattga                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 10
gggctgggga ggtgtttgtt                                                  20

<210> SEQ ID NO 11
<211> LENGTH: 20
<212> TYPE: DNA
<213> ORGANISM: Artificial Sequence
```

```
<220> FEATURE:
<223> OTHER INFORMATION: Description of Artificial Sequence:synthetic
      oligonucleotide

<400> SEQUENCE: 11
cactgcgggg agggctgggg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 12
agccgtggcc ttaaaatttt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 13
attttcaggc ctccatatgg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 14
aagagagaga ccctgaacag                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 15
gataatgttc ttggttataa                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 16
atggggtgca caaactgggg                                              20

<210> SEQ ID NO 17
<211> LENGTH: 20
<212> TYPE: DNA
<213> ORGANISM: Artificial Sequence
<220> FEATURE:
```

```
<223> OTHER INFORMATION: Description of Artificial Sequence:synthetic
      oligonucleotide

<400> SEQUENCE: 17
gtcagccatg gtcccccccc                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 18
cgccgtggag tcgttgcccg                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 19
tcaaatggag gctgcccggc                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 20
tggaatcaga cacaagccgt                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 21
catcttgcgc gcggggagcc                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 22
tgcgcgcggg gagccggacc                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:synthetic
```

```
      oligonucleotide

<400> SEQUENCE: 23
cgagaggtgc cggccccggg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 24
ctctcctcgc cctcgctcgg                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 25
tggagtttgc attcacctac                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 26
aaaggcctct aagacaagct                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 27
gccagcatgt gcaccgtgaa                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 28 acacccccagg ctcaacgatg                                             20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide
```

<400> SEQUENCE: 29
ccgaagctta ctcacaattt                                           20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 30
acttagctct tgacttcggg                                           20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 31
atcctgcgga aaataaattg                                           20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 32
attttatttt gagcatgttc                                           20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 33
tttggggatg agggtgagca                                           20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 34
cccattccca caggcctgag                                           20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide -continued

<400> SEQUENCE: 35
cggagcgcgc caggcaggga                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 36
cctttcccca gaccagccat                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 37
ggccccagaa acgtagcagg                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 38
ggatcctgcc tttcttgggg                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 39
cagccatggc cccagaaacg                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 40
cgacatgccg gcgccgctgc                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 41
cagacgacat gccggcgccg                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:synthetic
     oligonucleotide

<400> SEQUENCE: 42
gcctgcttcg cagcgggaga                                                  20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:synthetic
     oligonucleotide

<400> SEQUENCE: 43
acaggtgcag gagtcgaggc                                                  20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:synthetic
     oligonucleotide

<400> SEQUENCE: 44
gtcccgtctc aggccagccc                                                  20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:synthetic
     oligonucleotide

<400> SEQUENCE: 45
cctcaccgat gcggaccctc                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:synthetic
     oligonucleotide

<400> SEQUENCE: 46
attgaacttc atggtgccag                                                  20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:synthetic
     oligonucleotide

<400> SEQUENCE: 47
tctcactccc cataaggcta                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 48
ttcctttggg ttctcgtgcc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 49
ttccatcctt cgacagagtt                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 50
aggctgatgc tgggaaggtc                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 51
gttctaaggc tgatgctggg                                              20

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: modified_base
<222> LOCATION: (1)..(18)
<223> OTHER INFORMATION: oligo prepared with 2'propoxy nucleotides at
      positions 1-4 and 15-18; P=S linkages at bases
      1-18.
<220> FEATURE:
<221> NAME/KEY: modified_base
<222> LOCATION: (1)..(18)
<223> OTHER INFORMATION: another oligo prepared with 2'propoxy
      nucleotides at positions 1-4 and 15-18; P=O linkages at bases
      1-3 and 15-17; P=S linkages at bases 4-14.

<400> SEQUENCE: 52
ttctcgctgg tgagtttc                                                18

-continued

```
<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: modified_base
<222> LOCATION: (1)..(17)
<223> OTHER INFORMATION: 2'propoxy nucleotides at positions 1-3 and
      13-17; P=S linkages at bases 1-17.
<220> FEATURE:
<221> NAME/KEY: modified_base
<222> LOCATION: (1)..(17)
<223> OTHER INFORMATION: another oligo prepared with 2'propoxy
      nucleotides at positions 1-3 and 13-17; P=O linkage at
      positions 1-3 and 14-16; P=S linkages at bases 4-13.
<400> SEQUENCE: 53
tctcgctggt gagtttc                                                17
```

PHARMACEUTICAL COMPOSITIONS

This invention relates to pharmaceutical compositions, particularly liposomal oligonucleotide compositions, their preparation and their use.

In WO 95/02069 there are described oligonucleotides specifically hybridizable with DNA or RNA derived from a protein kinase C (PKC) gene, which oligonucleotides are particularly for use in the diagnosis and treatment of neoplastic, hyperproliferative and inflammatory disorders associated with protein kinase C.

It has now been found that compositions retaining high activity after prolonged circulation in the bloodstream and exhibiting reduced accumulation of oligonucleotide in non-target organs such as the liver and kidney can be prepared by formulation of such oligonucleotides within sterically stabilised liposomes.

Accordingly, the present invention provides a pharmaceutical composition comprising (A) an oligonucleotide having 5 to 50 nucleotide units specifically hybridizable with DNA or RNA derived from a protein kinase C gene, entrapped in (B) sterically stabilised liposomes.

Hybridisation, in the context of nucleic acid chemistry, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementary such that stable and specific binding occurs between the DNA or RNA target and the oligonucleotide. It is understood that an oligonucleotide need not be 100% complementary to its target nucleic acid sequence to be specifically hybridizable.

An oligonucleotide is specifically hybridizable when binding of the oligonucleotide to the target interferes with the normal function of the target molecule to cause a loss of utility, and there is a sufficient degree of complementary to avoid non-specific binding of the oligonucleotide to non-target sequences under conditions in which specific binding is desired, i.e. under physiological conditions in the case of in vivo assays or therapeutic treatment, or, in the case of in vitro assays, under conditions in which the assays are conducted.

As used in the context of this invention, the term "oligonucleotide" refers to a substance having a plurality of nucleotide units formed from naturally occurring bases and sugars joined by phosphodiester internucleoside (backbone) linkages. The term "oligonucleotide" also includes analogues which function similarly to naturally occurring oligonucleotides but which have non-naturally occurring monomers (nucleotides) or portions thereof. These oligonucleotide analogues are often preferred over native forms because of properties such as enhanced cellular uptake, enhanced target binding affinity and increased stability in the presence of nucleases.

In preferred embodiments of the invention, the oligonucleotide (A) is specifically hybridizable with the translation initiation codon of the PKC gene, in which case it preferably comprises a CAT sequence, or with the 5' untranslated region or 3' untranslated region of the gene. In other preferred embodiments of the invention, the oligonucleotide (A) is specifically hybridizable with DNA or mRNA encoding a particular PKC isozyme (isoform) or a particular set of PKC isozymes.

The oligonucleotide (A) preferably comprises from 8 to 30 nucleotide units, more preferably 12 to 25 nucleotide units, especially 18 to 22 nucleotide units.

In some preferred oligonucleotides (A), at least one nucleotide is modified at the 2' position of the sugar moiety. Certain preferred oligonucleotides (A) are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one preferred embodiment, a chimeric oligonucleotide comprises at least one region modified to increase target binding affinity and, usually, a region that acts as a substrate for RNAse H. Affinity of an oligonucleotide for its target is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase target binding affinity comprises at least one nucleotide modified at the 2' position of the sugar, particularly a 2'-alkoxy, 2'-alkoxyalkoxy or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. In the chimeric oligonucleotides, the region which is a substrate for RNAse H comprises at least one 2'-deoxynucleotide. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides may contain phosphorothioate, phosphotriester, methyl phosphonate, short chain alkyl or cycloalkyl intersugar linkages or short chain heteroatomic or heterocyclic intersugar ("backbone") linkages, e.g. amide-type linkages. Most preferred are phosphorothioates and those with $CH_2$—NH—O—$CH_2$, $CH_2$—$N(CH_3)$—O—$CH_2$, $CH_2$—O—$N(CH_3)$—

$CH_2$, $CH_2$—$N(CH_3)$—$N(CH_3)$—$CH_2$ and O—$N(CH_3)$—$CH_2$—$CH_2$ and $CH_2$—C(O)—NH—$CH_2$ backbones (where phosphodiester is O—P—O—$CH_2$). Also preferred are oligonucleotides having morpholino backbone structures, for example as described in U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone, as described by P. E. Nielsen, M. Egholm, R. H. Berg, O. Buchardt, Science 1991, 254, 1497. Other preferred oligonucleotides may contain sugar moieties comprising one of the following at the 2' position: OH; SH; $SCH_3$; F; OCN; $OCH_2OCH_3$; $O(CH_2CH_2)_mOCH_3$ wherein m is 1, 2 or 3, preferably $OCH_2CH_2OCH_3$; $OCH_2O(CH_2)_nCH_3$; $O(CH_2)_nNH_2$ or $O(CH_2)_nCH_3$ where n is from 1 to about 10; $OCH_2CH_2NR_1R_2$ wherein $R_1$ and $R_2$ are independently of each other, H or $CH_3$. $C_1$ to $C_{10}$ lower alkyl, substituted lower alkyl, alkaryl or aralkyl; $C_{1-10}$ lower alkoxy or substituted alkoxy, preferably $OCH_3$; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine. Preferred bases includexanthine, hypoxanthine, adenine, 2-aminoadenine, guanine, 6-thioguanine, uracil, thymine, cytosine, 5-methylcytosine, 5-propynyluracil, 5-fluorouracil and 5-propynylcytosine.

In certain especially preferred embodiments of the invention, all nucleotides of the oligonucleotide (A) are 2'-deoxynucleotides and all backbone linkages are phosphorothioate linkages.

In certain other especially preferred embodiments, the oligonucleotide (A) is a chimeric oligonucleotide having one or more regions with 2'-deoxynucleotides and one or more regions with 2'-modified nucleotides, preferably 2'-alkoxynucleotides or 2'-alkoxyalkoxynucleotides, particularly 2'-methoxyethoxynucleotides, the one or more 2'-deoxynucleotide regions preferably having phosphorothioate backbone linkages and the one or more 2'-modified nucleotide regions preferably having phosphodiester or phosphorothioate backbone linkages. These chimeric oligonucleotides preferably comprise a region of 2'-deoxynucleotides between two regions of 2'-modified nucleotides, the deoxynucleotide region being preferably at least 4 nucleotides long, more preferably at least 6 nucleotides long, especially at least 8 nucleotides long.

The oligonucleotides used as component (A) of the composition of the invention may be conveniently and routinely made using well-known techniques such as solid phase synthesis. Equipment for such synthesis is available commercially from various sources including Applied Biosystems. The use of such techniques to prepare oligonucleotides such as the phosphorothioates and alkylated derivatives is well known. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labelled, biotinylated or other modified oligonucleotides such as cholesterol-modified oligonucleotides.

Specific especially preferred oligonucleotides, for which the nucleotide sequences and preparation have been published in WO95/02069, include the following:

| No | Sequence | Target | Seq. ID No. |
|---|---|---|---|
| Oligonucleotides TarGeted to the Human PKC-α isozyme | | | |
| ON1 | CCC CAA CCA CCT CTT GCT CC | 5' Untranslated | 1 |
| ON2 | GTT CTC GCT GGT GAG TTT CA | 3' Untranslated | 2 |
| ON3 | AAA ACG TCA GCC ATG GTC CC | Translation init. codon | 3 |
| ON4 | GGA TTC ACT TCC ACT GCG GG | 3' Untranslated | 4 |
| ON5 | GAG ACC CTG AAC AGT TGA TC | 3' Untranslated | 5 |
| ON6 | CCC GGG AAA ACG TCA GCC AT | Translation init codon | 6 |
| ON7 | CTG CCT CAG CGC CCC TTT GC | Internal (C1) domain | 7 |
| ON8 | AGT CGG TGC AGT GGC TGG AG | Internal (C1) domain | 8 |
| ON9 | GCA GAG GCT GGG GAC ATT GA | Internal (C1) domain | 9 |
| ON10 | GGG CTG GGG AGG TGT TTG TT | 3' Untranslated | 10 |
| ON11 | CAC TGC GGG GAG GGC TGG GG | 3' Untranslated | 11 |
| ON12 | AGC CGT GGC CTT AAA ATT TT | 3' Untranslated | 12 |
| ON13 | ATT TTC AGG CCT CCA TAT GG | 3' Untranslated | 13 |
| ON14 | AAG AGA GAG ACC CTG AAC AG | 3' Untranslated | 14 |
| ON15 | GAT AAT GTT CTT GGT TGT AA | 3' Untranslated | 15 |
| ON16 | ATG GGG TGC ACA AAC TGG GG | Internal (C3) domain | 16 |
| ON17 | GTC AGC CAT GGT CCC CCC CC | Translation init. codon | 17 |
| ON18 | CGC CGT GGA GTC GTT GCC CG | Internal (V1) domain | 18 |
| ON19 | TCA AAT GGA GGC TGC CCG GC | Internal (C3) domain | 19 |
| ON20 | TGG AAT CAG ACA CAA GCC GT | 3' Untranslated | 20 |
| OLIGONUCLEOTIDES TARGETED TO PKC-β TYPES I AND II | | | |
| ON21 | CAT CTT GCG CGC GGG GAG CC | Translation init. | 21 |
| ON22 | TGC GCG CGG GGA GCC GGA CC | Translation init. | 22 |
| ON23 | CGA GAG GTG CCG GCC CCG GG | Translation init. | 23 |
| ON24 | CTC TCC TCG CCC TCG CTC GG | Translation init. | 24 |
| OLIGONUCLEOTIDES TARGETED TO PKC-β TYPE 1 | | | |
| ON25 | TGG AGT TTG CAT TCA CCT AC | 3' Untranslated | 25 |
| ON26 | AAA GGC CTC TAA GAC AAG CT | 3' Untranslated | 26 |
| ON27 | GCC AGC ATG TGC ACC GTG AA | 3' Untranslated | 27 |
| ON28 | ACA CCC CAG GCT CAA CGA TG | 3' Untranslated | 28 |
| ON29 | CCG AAG CTT ACT CAC AAT TT | 3' Untranslated | 29 |

OLIGONUCLEOTIDES TARGETED TO PKC-β TYPE II

| | | | | | | | |
|---|---|---|---|---|---|---|---|
| ON30 | ACT TAG CTC TTG ACT TCG GG | 3' Untranslated | 30 |
| ON31 | ATG CTG CGG AAA ATA AAT TG | 3' Untranslated | 31 |
| ON32 | ATT TTA TTT TGA GCA TGT TC | 3' Untranslated | 32 |
| ON33 | TTT GGG GAT GAG GGT GAG CA | 3' Untranslated | 33 |
| ON34 | CCC ATT CCC ACA GGC CTG AG | 3' Untranslated | 34 |

OLIGONUCLEOTIDES TARGETED TO PKC-γ

| | | | |
|---|---|---|---|
| ON35 | CGG AGC GCG CCA GGC AGG GA | 5' Untranslated | 35 |
| ON36 | CCT TTT CCC AGA CCA GCC AT | Translation init. | 36 |
| ON37 | GGC CCC AGA AAC GTA GCA GG | 5'of start codon | 37 |
| ON38 | GGA TCC TGC CTT TCT TGG GG | 5' Untranslated | 38 |
| ON39 | CAG CCA TGG CCC CAG AAA CG | Translation init. | 39 |

OLIGONUCLEOTIDES TARGETED TO PKC-η

| | | | |
|---|---|---|---|
| ON40 | CGA CAT GCC GGC GCC GCT GC | Translation init. | 40 |
| ON41 | CAG ACG ACA TGC CGG CGC CG | Translation init. | 41 |
| ON42 | GCC TGC TTC GCA GCG GGA GA | Translation init. | 42 |
| ON43 | ACA GGT GCA GGA GTC GAG GC | Translation init. | 43 |
| ON44 | GTC CCG TCT CAG GCC AGC CC | Translation init. | 44 |
| ON45 | CCT CAC CGA TGC GGA CCC TC | Translation init. | 45 |
| ON46 | ATT GAA CTT CAT GGT GCC AG | Translation init. | 46 |
| ON47 | TCT CAC TCC CCA TAA GGC TA | 3' Untranslated | 47 |
| ON48 | TTC CTT TGG GTT CTC GTG CC | 3' Untranslated | 48 |
| ON49 | TTC CAT CCT TCG ACA GAG TT | 3' Untranslated | 49 |
| ON50 | AGG CTG ATG CTG GGA AGG TC | 3' Untranslated | 50 |
| ON51 | GTT CTA AGG CTG ATG CTG GG | 3' Untranslated | 51 |

Chimeric 2'methoxy/deoxy P = S oligonucleotides;
underlined = 2'- methoxy; s = P = S linkage;
o = P = O linkage:

| NO. | SEQUENCE | SEQ ID NO. |
|---|---|---|
| ON52 | <u>AsAsAsAsCsGs</u>TsCsAsGsCsCsAsTs<u>GsGsTsCsCsC</u> | 3 |
| ON53 | <u>AoAoAoAoCoGs</u>TsCsAsGsCsCsAsTs<u>GoGoToCoCoC</u> | 3 |
| ON54 | <u>AsAoAoAoCoGs</u>TsCsAsGsCsCsAsTs<u>GoGoToCoCsC</u> | 3 |
| ON55 | <u>AsAoAoAoCoGs</u>ToCsAoGsCoCsAsTs<u>GoGoToCoCsC</u> | 3 |

Chimeric 2'-propoxy/deoxy P = S oligonucleotides;
underlined = 2'-propoxy; s = P = S linkage,
o = P = O linkage:

| NO. | SEQUENCE | SEQ ID NO: |
|---|---|---|
| ON56 | <u>AsAsAsAsCsGs</u>TsCsAsGsCsCsAsTs<u>GsGsTsCsCsC</u> | 3 |
| ON57 | <u>AoAoAoAoCoGs</u>TsCsAsGsCsCsAsTs<u>GoGoToCoCoC</u> | 3 |
| ON58 | <u>AsAoAoAoCoGs</u>TsCsAsGsCsCsAsTs<u>GoGoToCoCsC</u> | 3 |
| ON59 | <u>AsAoAoAoCoGs</u>ToCsAoGsCoCsAsTs<u>GoGoToCoCsC</u> | 3 |

Chimeric 2'-propoxy/deoxy P = S oligonucleotides
targeted to PKC-α 3'-UTR; Underlined = 2'-propoxy;
s = P = S linkage, o = P = O linkage;

| NO. | SEQUENCE | SEQ ID NO: |
|---|---|---|
| ON60 | TsTsCsTsCsGsCsTsGsGsTsGsAsGs<u>TsTsTsC</u> | 52 |
| ON61 | ToToCoTsCsGsCsTsGsGsTsGsAsGs<u>ToToToC</u> | 52 |
| ON62 | TsCsTsCsGsCsTsGsGsTsGsAsGs<u>GsTsTsC</u> | 53 |
| ON65 | ToCoToCsGsCsTsGsGsTsGsAsGs<u>ToToToC</u> | 53 |

Most preferred among the oligonucleotides hereinbefore described are those having SEQUENCE ID No. 2,3 or 5.

In compositions of the invention, the oligonucleotide (A) is entrapped in sterically stabilised liposomes (B). Examples of sterically stabilised liposomes are those in which part of the lipid is a glycolipid, particularly ganglioside GM, saturated phosphatidylinositol or galactocerebroside sulphate ester, such as those described in WO 88/04924; those in which part of the lipid is derivatised with hydrophilic polymer such as those described in WO 91/05545 or U.S. Pat. No. 5,225,212; and those comprising a vesicle-forming lipid and a lipid-polymer conjugate having a hydrophobic moiety and a polar head group, such as those described in WO 94/20073.

In a preferred embodiment of the invention, the liposomes (B) comprise at least one underivatised vesicle-forming lipid and at least one vesicle-forming lipid derivatised with hydrophilic polymer which may be, for example, a polymer containing a hydroxy and/or carboxyl group such as a polylactic acid, a polyglycolic acid or, preferably, a polyethylene-glycol. More preferably, the hydrophilic polymer is a polyethyleneglycol having a molecular weight of 1000 to 5000 daltons, such as 1500 to 2500 daltons, especially 1800 to 2200 daltons. The hydrophilic polymer is preferably derivatised with a polar head group of a phospholipid, especially a phospholipid having an amino head group, i.e. the derivatised lipid is preferably a phospholipid having an amino group, especially a phosphatidylethanolamine such as dilauroyl phosphatidylethanolamine, dimyristoyl phosphatidylethanolamine, dioleoyl phosphatidylethanolamine or, particularly, distearoyl phosphatidylethanolamine.

Various methods of derivatising an amino-containing lipid with a hydroxyl- and/or carboxyl-containing hydrophilic polymer will be apparent to those skilled in the art. Several such methods are described in WO 91/05545 and U.S. Pat. No. 5,225,212; the phospholipid having an amino group may be derivatised with the hydrophilic polymer by any of these methods. Preferably, the phospholipid having an amino group is derivatised with a hydroxyl-containing hydrophilic polymer such that the polymer is attached to the phospholipid through a carbamate linkage; this may be achieved by reacting a hydroxyl group of the polymer (other hydroxyl groups being capped, if necessary in view of their reactivity, for example by etherification) with diimidazole to give an activated imidazole—terminated polymer which is then reacted with the amino-containing phospholipid to couple the phospholipid to the hydrophilic polymer through a carbamate group, as described in WO 91/05545 or U.S. Pat. No. 5,225,212. In an especially preferred embodiment of the invention, the derivatised lipid is an amino-containing phospholipid, particularly a phosphatidylethanolamine, coupled through a carbamate group to a polyethyleneglycol capped at one end by an alkoxy group, particularly a methoxy or ethoxy group. Such a derivatised lipid is available commercially.

The derivatised lipid is generally present in a minor molar amount relative to the total lipid content of the liposomes, preferably in an amount of 1 to 20 mole % of the total lipid content, although a lower amount, for example 0.1 mole %, may be appropriate when the derivatised lipid has a high molecular weight. The major part of the lipid content of the liposomes generally comprises one or more underivatised vesicle-forming lipids such as are used in conventional liposomes. Such lipids include, for example, lipids having two hydrocarbon chains, usually in acyl groups, and a polar head group, including phospholipids, for example phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, phosphatidylethanolamines such as those mentioned hereinbefore, and phosphatidic acids such as dimyristoyl phosphatidic acid and dipalmitoyl phosphatidic acid. Other conventionally used lipids include sterols, particularly cholesterol, and glycolipids such as those mentioned hereinbefore. Preferably, the underivatised lipid comprises a mixture of a phospholipid, especially a phosphatidylcholine, and a sterol, especially cholesterol.

In the abovementioned preferred embodiment, the sterically stabilised liposomes (B) preferably comprise 4–10 mol % of the derivatised lipid, 40–80 mol % of the underivatised phospholipid and 20–50 mol % of the sterol. In especially preferred liposomes (B), the molar ratio of derivatised lipid: underivatised phospholipid: sterol is 1:10:5.

In another preferred embodiment of the invention, the liposomes (B) comprise (i) a glycolipid together with (ii) a vesicle-forming phospholipid or sphingolipid or mixture thereof and, optionally, (iii) a sterol and/or an acylglycerol lipid. The glycolipid is preferably a negatively charged glycolipid, especially ganglioside $GM_1$ (monosialoganglioside) or hydrogenated phosphatidylinositol. The vesicle-forming phospholipid may be one or more of the phospholipids hereinbefore mentioned, preferably a phosphatidylcholine, a phosphatidylethanolamine or a mixture thereof. Especially preferred phospholipids are distearoyl phosphatidylcholine and dioleoyl phosphatidylethanolamine. The sphingolipid is preferably sphingomyelin and is preferably used together with a phospholipid. The sterol may be, for example, ergosterol or, preferably, cholesterol. The acylglycerol lipid may be an ester of glycerol containing two fatty acid acyl groups each having at least 12 carbon atoms, for example lauroyl, myristoyl, palmitoyl or oleoyl groups, and one acyl group of formula $R^1CO-$, where $R^1$ is a residue, containing up to 10 carbon atoms, of a monocarboxylic acid of formula $R^1COOH$ after removal of the $-COOH$ group or, preferably, of formula $-COR^2COOH$ where $R^2$ is a residue, containing up to 10 carbon atoms, preferably 1 to 4 carbon atoms, of a dicarboxylic acid of formula $HOOC-R^2-COOH$, especially succinic acid, after removal of both $-COOH$ groups. An especially preferred acylglycerol is 1,2-dipalmitoyl-sn-3-succinylglycerol.

In this second preferred embodiment of the invention, the liposomes preferably comprise (i) a negatively charged glycolipid together with (ii) a vesicle-forming phospholipid and/or sphingolipid and (iii) a sterol or acylglycerol lipid, especially (i) ganglioside $GM_1$ or hydrogenated phosphatidylinositol together with (ii) distearoyl phosphatidylcholine or dioleoyl phosphatidylethanolamine or a mixture thereof with sphingomyelin and (iii) cholesterol or 1,2-dipalmitoyl-sn-3-succinylglycerol.

The liposomes may comprise from 2 to 20 mol % of the glycolipid (i) and 80 to 98 mol % of (ii) the phospholipid, sphingolipid or mixture thereof. In preferred embodiments, where the liposomes also comprise a sterol or acylglycerol, they may comprise 2 to 20 mol %, preferably 4 to 10 mol %, of the glycolipid, 40 to 80 mol %, preferably 60 to 80 mol %, of the phospholipid, sphingolipid or mixture thereof and 10 to 50 mol %, preferably 20 to 40 mol %, of the sterol or 5 to 40 mol %, preferably 10 to 30 mol %, of the acylglycerol.

Specific especially preferred liposomes (B) are those described hereinafter in the Examples.

The oligonucleotide-containing liposomes of the invention can be prepared using known methods for the preparation of drug-containing liposomes. For example, in one method, the lipid composition is dissolved in an organic solvent, such as an alcohol, ether, halohydrocarbon or mixture thereof, the solvent is removed from the resulting solution, for example by rotary evaporation or freeze drying, and the resulting lipid film is hydrated by dispersing in an aqueous medium, such as phosphate-buffered saline or an aqueous solution of a sugar, e.g. lactose, which medium also contains the oligonucleotide (A), to give an aqueous suspension of liposomes in the form of multilamellar vesicles (MLV's). The aqueous liposome suspension may be treated to reduce the liposome size, for example to give small unilamellar vesicles (SUV's), using known methods, for example by sonication or by extrusion through one or more membranes, e.g. polycarbonate membranes, having a selected pore size. Liposomes according to the invention preferably have on average a particle size below 500 nm, more preferably 50 to 200 nm, especially 80 to 120 nm.

It is generally desirable to have as high a weight ratio of oligonucleotide to lipid as possible consistent with liposome stability. The maximum for this weight ratio may vary depending on the nature and composition of the lipid component, but in general this maximum is likely to be about 1:20. Ratios between 1:40 and 1:400 can be used with good results.

The invention includes a method of modulating the expression of protein kinase C in cells which comprises contacting the cells with a composition of the invention as hereinbefore defined. The invention also includes a method of treating a condition associated with expression of protein kinase C which comprises administering a composition of the invention as hereinbefore defined to a mammal, particularly a human, or cells thereof, in need of such treatment.

The composition of the invention may be administered by pulmonary delivery or, preferably, parenterally, for example intravenously, subcutaneously, intraperitoneally or intramuscularly. Conditions which may be treated with the composition include hyperproliferative disorders such as psoriasis and mammalian cancer, particularly human cancer such as lung cancer, breast cancer, colorectal cancer and skin cancer.

For these indications, the appropriate dosage will, of course, vary depending upon the method of administration and on the severity and responsiveness of the condition to be treated. Individual doses and the administration regime can best be determined by individual judgement of a particular case of illness. However, in general, satisfactory results in animals are indicated to be obtained at daily dosages from about 0.6 mg/kg to about 6 mg/kg.

In larger mammals, for example humans, an indicated daily dose in the range of about 4.2 mg to about 420 mg conveniently administered, for example in divided doses of up to 3 times per day.

The invention is illustrated by the following Examples.

EXAMPLE 1

A derivatised lipid, prepared by coupling distearoyl phosphatidylethanolamine to a methoxy-capped polyethylene glycol of molecular weight 2000 through a carbamate group (DSPE-MPEG 2000 available from Genzyme), distearoyl phosphatidylcholine (available from Sigma Chemical) and cholesterol are dissolved, at a molar ratio of 1:10:5, in chloroform. The solvent is removed by rotary evaporation to leave a lipid film. This film (250 mg) is hydrated with Hanks' balanced salt solution (2 ml) buffered to pH 7.4 with 25 mM 4-(2-hydroxyethyl)piperazine-1-ethane sulphonic acid (HEPES) and containing oligonucleotide ON2 as hereinbefore defined (5 mg) in tritiated form. The resulting MLV's are subjected to ten liquid nitrogen-water freeze-thaw cycles and then sonicated (wavelength 6 μm) for 2 minutes to give small unilamellar vesicles (SUVs) having an average diameter of 80 to 100 nm. The resulting sterically stabilised liposomes are purified to remove unentrapped oligonucleotide by size exclusion chromatography using a Sephadex G-150 column and a 25 mM sodium borate elution buffer.

The liposomes are subjected to pharmacokinetic testing as follows: male Wistar rats (240–270 g) are fed ad libitum with a standard laboratory diet (Rat and Mouse diet, Bantin and Kingman, Hull, UK) and kept under controlled conditions (12 hour light cycle; 20° C.). The animals are lightly sedated by intramuscular injection of 20 ml fentanyl (Hyponorm, Janssen Pharmaceuticals Ltd, Oxford UK) to immobilise them. A suspension of the tritiated oligonucleotide—containing liposomes in phosphate buffered saline, containing 1.0 μCi of the tritiated oligonucleotide, is administered to the rats by tail vein injection. The rats are then maintained in metabolism cages for up to 48 hours with free access to food and water. Animals are sacrificed at intervals of 6, 12, 24 and 48 hours by overdosing with sodium pentabarbitone. The organs of interest are collected, weighed and their [$^3$H] content determined by combustion in a tissue oxidiser followed by liquid scintillation counting (LS 6500; Beckman Instruments, UK). The [$^3$H] content of each sample is adjusted for total tissue weight and expressed as a percentage of the dose administered to each animal.

The above test procedure is repeated, using a solution of the tritiated oligonucleotide ON2, instead of liposomes containing tritiated ON2, in phosphate buffered saline.

The test results (average for 3 animals) are as follows:

| Tissue | 6 hour | 12 hour | 24 hour | 48 hour |
| --- | --- | --- | --- | --- |
| Percentage dose of [3H] ON2 in tissues after dosing in solution | | | | |
| urine | 0.99 | 1.77 | 3.24 | 6.53 |
| liver | 40.54 | 35.00 | 45.47 | 35.16 |
| kidney | 9.24 | 7.48 | 10.39 | 13.04 |
| spleen | 1.66 | 1.05 | 1.48 | 1.48 |
| heart | 0.03 | 0.02 | 0.05 | 0.03 |
| muscle | 3.99 | 1.80 | 4.09 | 3.07 |
| skin | 2.05 | 1.06 | 2.53 | 1.62 |
| bone | 17.00 | 11.59 | 14.70 | 16.15 |
| fat | 0.44 | 0.08 | 0.13 | 0.46 |
| Percentage dose of [3H] ON2 in tissues after dosing in Sterically Stabilised Liposomes | | | | |
| urine | 0.03 | 0.12 | 0.47 | 1.67 |
| liver | 9.88 | 10.16 | 9.26 | 7.83 |
| kidney | 1.40 | 0.91 | 1.28 | 1.05 |
| spleen | 18.02 | 22.48 | 23.41 | 20.51 |
| heart | 0.44 | 0.43 | 0.36 | 0.31 |
| muscle | 8.09 | 13.07 | 31.47 | 27.81 |
| skin | 2.95 | 1.91 | 2.82 | 2.03 |
| bone | 6.52 | 6.06 | 9.89 | 6.61 |
| fat | 1.93 | 1.98 | 1.77 | 0.84 |

We claim:

1. A pharmaceutical composition comprising:
   (A) an oligonucleotide comprising 5 to 50 nucleotide units, which is specifically hybridizable with DNA or RNA derived from an isoform of the human protein kinase C gene, entrapped in
   (B) sterically stabilized liposomes that include a glycolipid or sterically stabilized liposomes that include a lipid derivatized with a hydrophilic polymer.

2. The pharmaceutical composition of claim 1 wherein the oligonucleotide (A) specifically hybridizes to a translation initiation site, a 5' untranslated region or a 3' untranslated region of an isoform of the human protein kinase C gene.

3. A composition according to claim 1 wherein the oligonucleotide (A) has 8 to 30 nucleotide units.

4. A composition according to claim 3, wherein the oligonucleotide (A) has 12 to 25 nucleotide units.

5. A composition according to claim 4, wherein the oligonucleotide (A) has 18 to 22 nucleotide units.

6. A composition according to claim 1 wherein at least one nucleotide of the oligonucleotide (A) is modified at the 2' position of the sugar moiety.

7. A composition according to claim 1 wherein the oligonucleotide (A) is a chimeric oligonucleotide which contains a first region having at least one nucleotide modified to enhance target affinity and a second region which is a substrate for RNAse H.

8. A composition according to claim 7, wherein a nucleotide modified to enhance target affinity is modified at the 2' position of the sugar moiety.

9. A composition according to claim 6 wherein the modified nucleotide has an alkoxy, alkoxyalkoxy or fluoro substituent at the 2' position.

10. A composition according to claim 7 wherein the oligonucleotide (A) is a chimeric oligonucleotide and the region which is a substrate for RNAse H comprises at least one 2'-deoxynucleotide.

11. A composition according to claim 1 wherein the oligonucleotide (A) has at least one phosphorothioate linkage.

12. A composition according to claim 1, wherein, in the oligonucleotide (A), all nucleotides are 2'-deoxynucleotides and all backbone linkages are phosphorothioate linkages.

13. A composition according to claim 1 wherein the oligonucleotide (A) is a chimeric oligonucleotide having one or more regions with 2'-deoxynucleotides and one or more regions with 2'-alkoxynucleotides or 2'-alkoxyalkoxynucleotides.

14. A composition according to claim 13, in which the 2'-alkoxyalkoxynucleotides are 2'-methoxyethoxynucleotides.

15. A composition according to claim 13 wherein the one or more regions with 2'-deoxynucleotides have phosphorothioate backbone linkages and the one or more regions with 2'-alkoxynucleotides or 2'-alkoxyalkoxynucleotides have phosphodiester or phosphorothioate backbone linkages.

16. A composition according to claim 13 wherein the oligonucleotide (A) comprises a region of 2'-deoxynucleotides between two regions of 2'-alkoxynucleotides or 2'-alkoxyalkoxynucleotides.

17. A composition according to claim 16, wherein the deoxynucleotide region has at least 4 nucleotides.

18. A composition according to claim 17, wherein the deoxynucleotide region has at least 6 nucleotides.

19. A composition according to claim 18, wherein the deoxynucleotide region has at least 8 nucleotides.

20. The pharmaceutical composition of claim 1 wherein the oligonucleotide (A) specifically hybridizes to human PKC-α.

21. A composition according to claim 1 wherein the oligonucleotide (A) comprises a nucleotide sequence selected from SEQ. ID Nos. 1 to 53.

22. A composition according to claim 1 wherein the oligonucleotide (A) comprises a nucleotide sequence selected from SEQ. ID Nos. 2, 3 and 5.

23. A composition according to claim 1 wherein the liposomes (B) comprise at least one underivatised vesicle-forming lipid and at least one vesicle-forming lipid which is derivatised with a hydrophilic polymer.

24. A composition according to claim 23, wherein the hydrophilic polymer is a polyethyleneglycol.

25. A composition according to claim 23 wherein the derivatised lipid is a phospholipid having an amino group.

26. A composition according to claim 25, wherein the hydrophilic polymer is attached to the phospholipid through a carbamate linkage.

27. A composition according to claim 25 wherein the amino-containing phospholipid is a phosphatidylethanolamine.

28. A composition according to claim 27, wherein the amino-containing phospholipid is distearoyl phosphatidylethanolamine.

29. A composition according to claim 23 wherein the derivatised lipid comprises 1–20 mole % of the total lipid content of the liposomes.

30. A composition according to claim 23 wherein the underivatised lipid is a lipid having two hydrocarbon chains and a polar head group and/or a sterol.

31. A composition according to claim 30, wherein the lipid having two hydrocarbon chains and a polar head group is a phosphatidylcholine.

32. A composition according to claim 31, wherein the phosphatidylcholine is distearoyl phosphatidylcholine.

33. A composition according to claim 30 wherein the sterol is cholesterol.

34. A composition according to claim 23 wherein the liposomes comprise 4–10 mol % derivatised lipid, 40–80 mol % underivatised lipid and 20–50 mol % sterol.

35. A composition according to claim 34, wherein the molar ratio of derivatised lipid: underivatised lipid: sterol is 1:10:5.

36. A pharmaceutical composition comprising:
   an oligonucleotide comprising 5 to 50 nucleotide units, which is specifically hybridizable with DNA or RNA derived from an isoform of the human protein kinase C gene, entrapped in liposomes comprising (i) a glycolipid together with (ii) a vesicle-forming phospholipid or sphingolipid or mixture thereof, and, optionally, (iii) a sterol and/or an acylglycerol lipid.

37. A composition according to claim 36, wherein the glycolipid is a negatively charged glycolipid.

38. A composition according to claim 37, wherein the liposomes comprise (i) a negatively charged glycolipid together with (ii) a vesicle-forming phospholipid and/or sphingolipid and (iii) a sterol or acylglycerol lipid.

39. A composition according to claim 37 wherein the glycolipid is ganglioside $GM_1$ or hydrogenated phosphatidylinositol.

40. A composition according to claim 36 wherein the vesicle-forming phospholipid is a phosphatidylcholine or a phosphatidylethanolamine.

41. A composition according to claim 40, wherein the phospholipid is distearoyl phosphatidylcholine or dioleoyl phosphatidylethanolamine.

42. A composition according to claim 36 wherein the sphingolipid is sphingomyelin.

43. A composition according to claim 36 wherein the acylglycerol lipid has two fatty acid acyl groups each having at least 12 carbon atoms and one acyl group of formula $R^1CO$—, where $R^1$ is a residue, containing up to 10 carbon atoms, of a monocarboxylic acid of formula $R^1COOH$ after removal of the —COOH group, or of formula $OC$—$R^2$—COOH where $R^2$ is a residue, containing up to 10 carbon atoms, of a dicarboxylic acid of formula HOOC—$R^2$—COOH after removal of both —COOH groups.

44. A composition according to claim 43, wherein the acylglycerol is 1,2-dipalmitoyl-sn-3-succinyl glycerol.

45. A composition according to claim 36 wherein the liposomes comprise 2 to 20 mol % of the glycolipid, 40 to 80 mol % of the phospholipid, sphingolipid or mixture thereof and 10 to 50 mol % of the sterol or 10 to 30 mol % of the acylglycerol.

46. A composition according to claim 45, wherein the liposomes comprise 4 to 10 mol % of the glycolipid, 60 to 80 mol % of the phospholipid, sphingolipid or mixture thereof and 20 to 40 mol % of the sterol or 10 to 30 mol % of the acylglycerol.

47. A composition according to claim 1 wherein the liposomes have an average particle size of 50 to 200 nm.

48. A composition according to claim 47, wherein the liposomes have an average particle size of 80 to 120 nm.

49. A method of inhibiting the expression of an isoform of human protein kinase C in cells comprising the step of contacting the cells with a composition comprising
   (A) an oligonucleotide comprising 5 to 50 nucleotide units, which specifically hybridizes to DNA or RNA derived from an isoform of human protein kinase C gene, entrapped in
   (B) sterically stabilized liposomes that include a glycolipid or sterically stabilized liposomes that include a lipid derivatized with a hydrophilic polymer.

50. A method of treating a hyperproliferative condition associated with expression of an isoform of human protein kinase C comprising the step of administering a composition comprising
   (A) an oligonucleotide comprising 5 to 50 nucleotide units, which specifically hybridizes to DNA or RNA derived from an isoform of human protein kinase C gene, entrapped in
   (B) sterically stabilized liposomes that include a glycolipid or sterically stabilized liposomes that include a lipid derivatized with a hydrophilic polymer; to a mammal, or cells thereof, in need of such treatment.

51. The pharmaceutical composition of claim 1 comprising sterically stabilized liposomes that include a glycolipid.

52. The pharmaceutical composition of claim 1 comprising sterically stabilized liposomes that include a lipid derivatized with a hydrophilic polymer.

53. The composition according to claim 1 further comprising liposomes comprising a vesicle-forming lipid and a lipid-polymer conjugate having a hydrophobic moiety and a polar head group.

* * * * *